United States Patent [19]

Zenkich

[11] Patent Number: 4,848,345
[45] Date of Patent: Jul. 18, 1989

[54] CONNECTION CIRCUIT AND METHOD FOR USING MONITOR/DEFIBRILLATOR

[75] Inventor: Ilias R. Zenkich, Norridge, Ill.

[73] Assignee: Zenex Corporation, Chicago, Ill.

[21] Appl. No.: 873,653

[22] Filed: Jan. 30, 1978

[51] Int. Cl.$^4$ .............................................. A61N 1/36
[52] U.S. Cl. .................................. 128/419 D; 128/639; 128/798
[58] Field of Search ............... 128/404, 416, 783, 417, 128/798, 418, 419 D; 639/206 E, 21 E; 642/DIG. 4

[56] References Cited

U.S. PATENT DOCUMENTS

| | | | |
|---|---|---|---|
| 3,386,445 | 6/1968 | McDonald | 128/417 |
| 3,716,059 | 2/1973 | Welborn et al. | 128/419 D |
| 3,814,105 | 6/1974 | Howard et al. | 128/419 D |
| 3,954,100 | 5/1976 | Sem-Jacobson | 128/2.06 E |
| 3,972,329 | 8/1976 | Kaufman | 128/2.06 E |
| 3,977,392 | 8/1976 | Manley | 128/4 D X |
| 4,030,596 | 6/1977 | Heilman et al. | 128/419 D |

FOREIGN PATENT DOCUMENTS 13888 10/1971 Australia ............................. 128/417

Primary Examiner—William E. Kamm
Attorney, Agent, or Firm—Wood, Dalton, Phillips, Mason & Rowe

[57] ABSTRACT

A circuit for connecting a monitor/defibrillator to a patient and a method for monitoring the condition of the heart and for selectively applying a pulse of energy to the patient for defibrillation. A first and a second electrode are adhesively secured to the patient. The electrodes form an assembly which is coupled to a connection circuit leading to the monitor/defibrillator. A switch module is mounted on the connection circuit and is positioned remotely from the patient. The switch module has a plurality of operator-actuated switches which, when depressed, cause the monitor/defibrillator to provide a pulse of energy to the electrodes for defibrillation. The switches are arranged so that both hands of the operator are required to simultaneously close them, thereby assuring that the ends of the operator are remote from the patient during defibrillation.

14 Claims, 2 Drawing Sheets

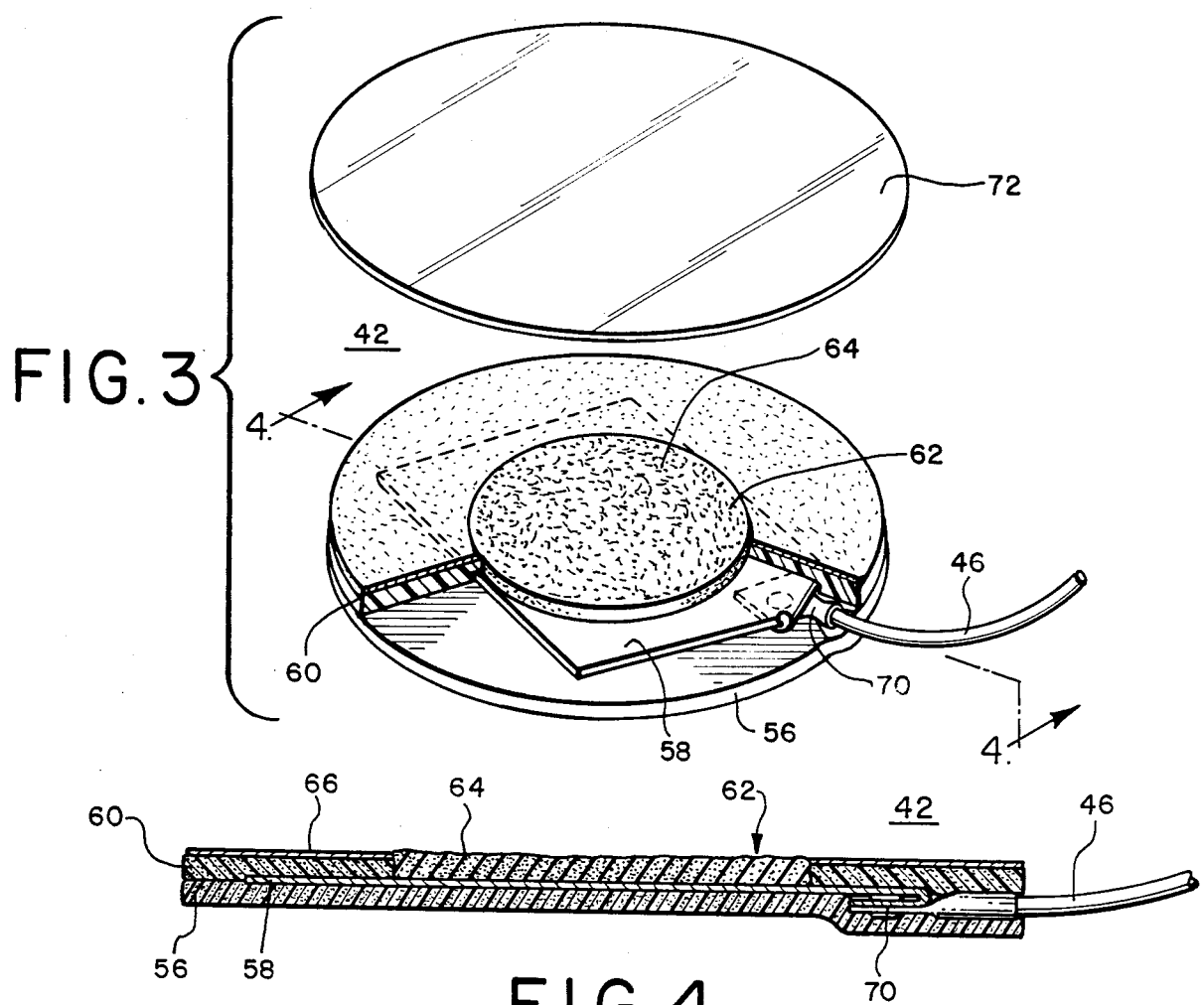
FIG. 3
FIG. 4
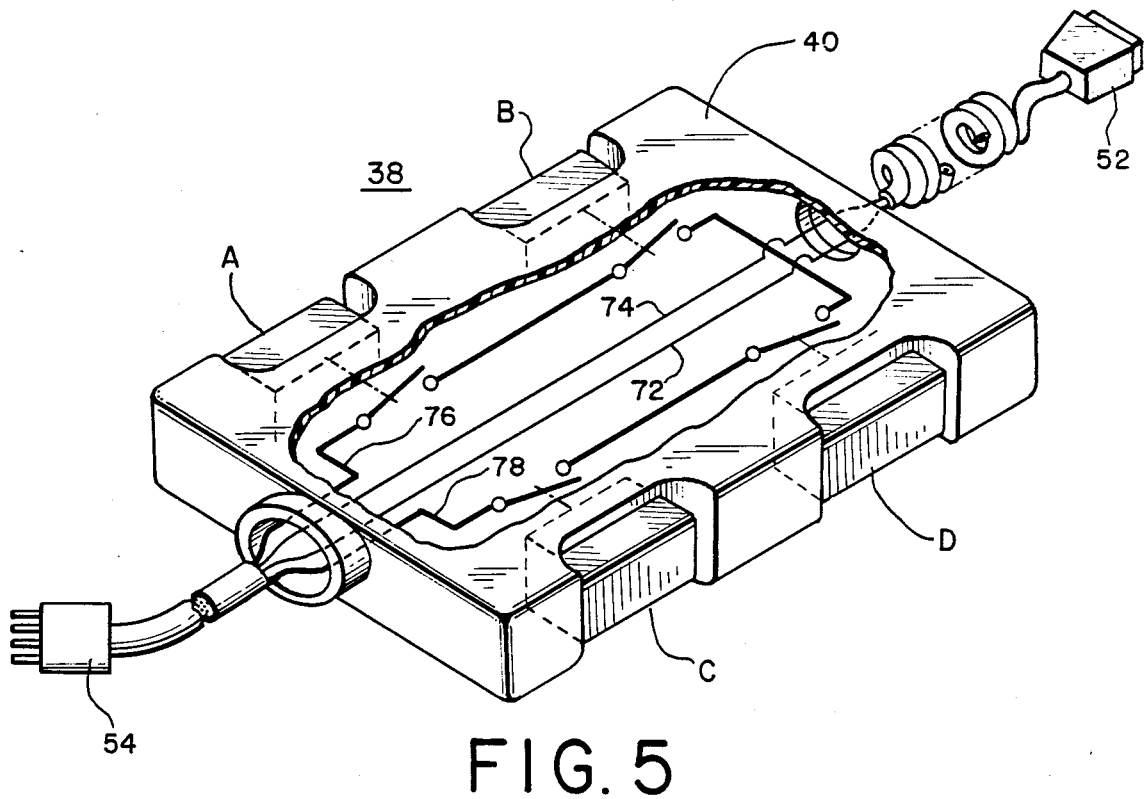
FIG. 5

CONNECTION CIRCUIT AND METHOD FOR USING MONITOR/DEFIBRILLATOR

BACKGROUND OF THE INVENTION

This invention relates to systems for monitoring and defibrillating the heart of a patient and, more particularly, to an improved circuit for connecting the patient to the monitor/defibrillator.

Emergency medical procedures often require that a physician or paramedic quickly prepare a patient for ECG monitoring and/or defibrillation if the need arises.

This procedure usually requires that monitoring electrodes be applied to the chest of the patient and connected to the monitor/defibrillator. If a pulse of energy is to be applied to the patient for defibrillation, additional large hand-held paddles from the monitor/defibrillator must be placed against the patient by the operator. This procedure results in the presence of many electrodes and tangled wires, and requires that the operator maintain the paddles against the patient during defibrillation.

If the operator, while maintaining the paddles against the patient, inadvertently touches him when the pulse of energy is delivered, the operator is likely to receive an electric shock.

SUMMARY OF THE INVENTION

In accordance with the present invention, an improved connection circuit between the patient and the monitor/defibrillator greatly simplifies emergency medical procedures involving monitoring and defibrillation of the heart. The circuit employs an improved electrode assembly having electrodes of sufficient size to monitor the heart and to apply a pulse of energy for defibrillation if required. A single pair of self-adhering electrodes is applied to the patient, and the operator need not hold them against the patient during defibrillation.

A switch module is mounted on the connection circuit remote from the patient. The switch module has four series-connected switches which when simultaneously depressed cause the monitor/defibrillator to provide a pulse of energy to the patient for defibrillation. The module is constructed and arranged so that both hands of the oeprator are required to simultaneously depress the four switches, thus assuring that the operator keeps his hands remote from the patient during defibrillation, thereby avoiding the possibility of shock.

It is a feature of the present invention to provide a system for connecting a monitor/defibrillator to a patient while avoiding tangled wires and hand-held paddles.

It is another feature of the invention to provide a system whih employs a single pair of electrodes for both defibrillating and monitoring the heart of the patient.

Yet another feature of the invention is to provide a disposable electrode assembly for emergency medical use which can be readily disconnected from the system.

Another feature of the present invention is to provide an operator-actuated switch module on the conductors from the electrode assembly to the monitor/defibrillator to assure that the operator's hands remain remote from said patient during defibrillation.

DRAWING

FIG. 3 is an exploded perspective view, partially in section, of an electrode shown in FIG. 2;

FIG. 4 is a cross-sectional view taken through the line 4—4 of the electrode shown in FIG. 3; and FIG. 5 is a perspective view of the switch module shown in FIG. 2 with a portion of the switch module broken away.

DESCRIPTION OF THE PREFERRED EMBODIMENT

Figure 1:
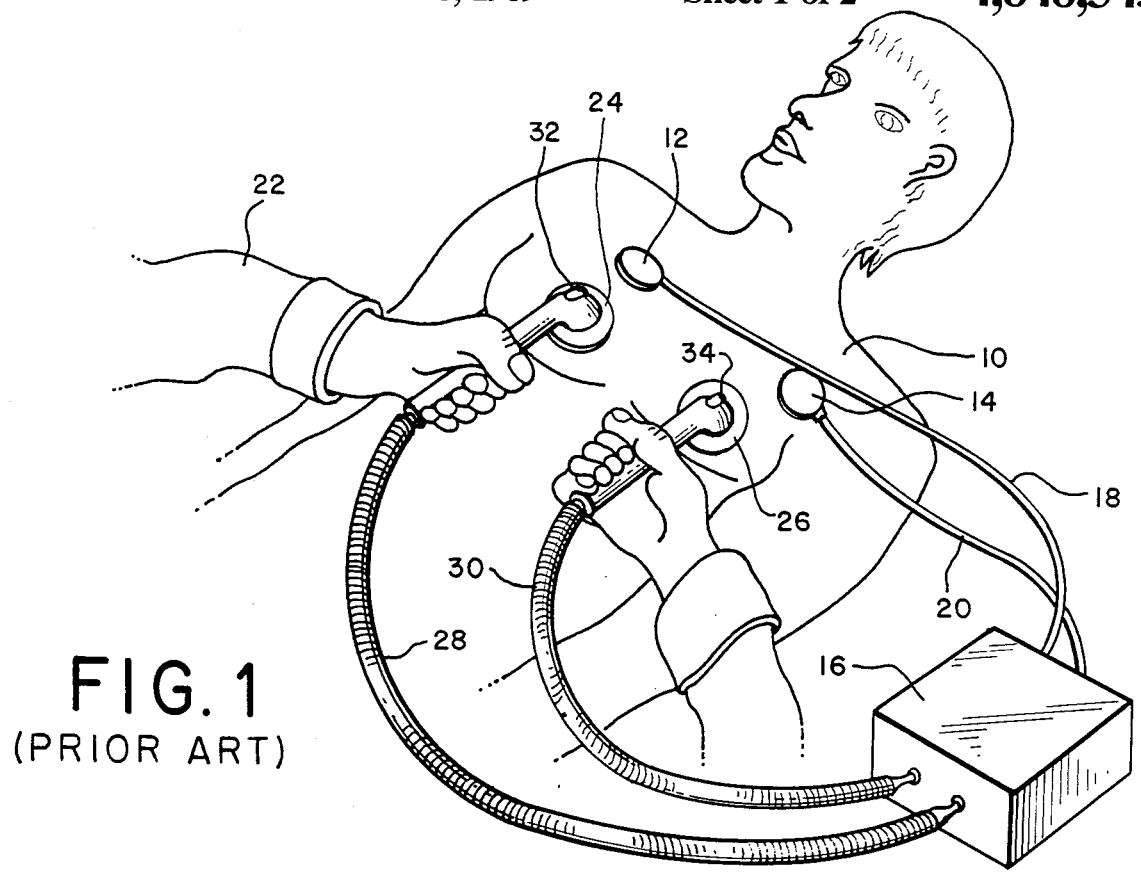
FIG. 1 is a perspective view of a monitor/defibrillator connected to a patient and known to the prior art.

Referring to FIG. 1, a rescue effort is being performed on patient 10. Monitor electrodes 12 and 14, secured to patient 10, are coupled to monitor/defibrillator 16 through leads 18 and 20, respectively. If defibrillation is required, operator 22 grasps hand-held paddles 24 and 26, each of which has a conductive undersurface (not shown) and applies them to the chest of patient 10. The hand-held paddles 24 and 26 are coupled to the monitor/defibrillator 16 through conductors 28 and 30, respectively. The monitor/defibrillator 16 may be provided with isolation circuitry to electrically disconnect the monitoring equipment from the circuit while the pulse of energy is applied to patient 10 for defibrillation.

If it is desired to apply a pulse of energy through paddles 24 and 26 to patient 10 to cause defibrillation, switches 32 and 34, located on hand-held paddles 24 and 26 respectively, are simultaneously depressed. Operator 22 must be careful not to inadvertently touch the body of patient 10 while depressing defibrillation switches 32 and 34.

Figure 2:
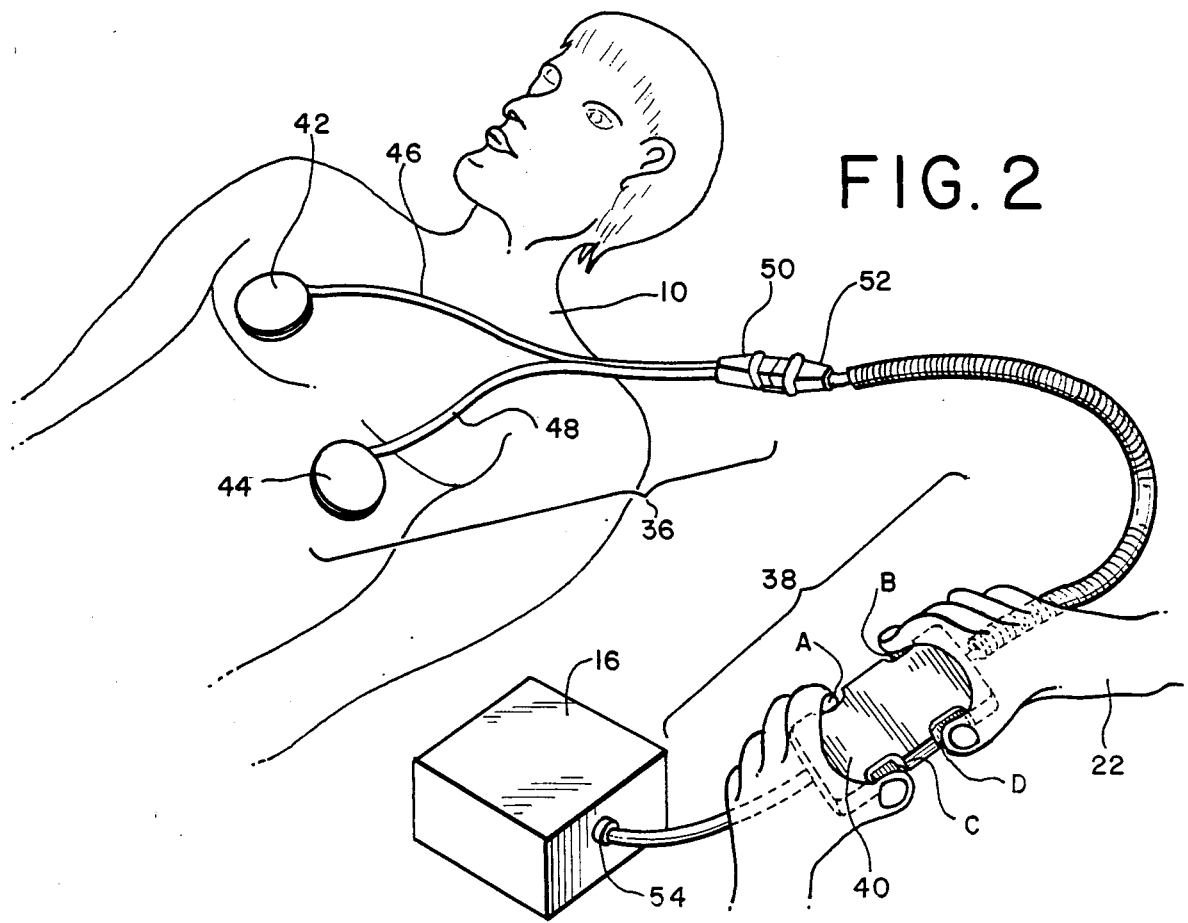
FIG. 2 is a perspective view of the monitor/defibrillator connected to a patient by the connection system in accordance with the present invention.

Referring to FIG. 2, the monitor/defibrillator of the present invention is shown to include a disposable electrode assembly 36 coupled to a connection circuit 38 which leads from the disposable electrode assembly 36 to the monitor/defibrillator 16. The connection circuit 38 includes a switch module 40 mounted on, but in electrical isolation with, the conductor from monitor/defibrillator 16 to disposable electrode assembly 36.

The disposable electrode assembly 36 includes similarly constructed electrodes 42 and 44 which, as will be explained in greater detail below, self-adhere to patient 10. Leads 46 and 48 from electrodes 42 and 44, respectively, are provided to connector 50. The configuration of connector 50 is selected to mate with connector 52 which is secured to connection circuit 38. It is noted that lead 46 is somewhat longer than lead 48. Although either lead can be of any selected length, it is particularly desirable to select one lead longer than the other to accommodate the across-the-chest positioning of the electrodes 42 and 44.

Connection circuit 38 connects the monitor/defibrillator 16 to the disposable electrode assembly 36. Connector 54 coupled the conductor 38 to the monitor/defibrillator 16. The shape and size of connector 54 is selected in accordance with the specific type of monitor/defibrillator to be employed.

Switch module 40 has a generally rectangular cross section of two sides, a top and a bottom. Four switches, A, B, C and D, are located on the sides of switch module 40. The switches A, B, C and D are located within switch module 40 so that both hands of operator 22 are required to simultaneously depress the four switches, thereby causing the electric shock to be delivered to the patient 10 while assuring that the hands of operator 22 are remotely positioned from said patient.

Referring to FIGS. 3 and 4, the construction of electrode 42, which is identical to electrode 44, will be explained. Electrode 42 has a base 56 of flexible insulating material to which is secured metallic foil 58. A cover 60 of insulating material is secured to the upper surface of base 56 and has an aperture 62 through which metal foil 58 is exposed. A conductive gel-impregnated sponge pad 64 is located in aperture 62 and engages a principal portion of the surface of the metallic foil 58. The conductive gel-impregnated sponge pad 64 affords a low resistance path and a good electrical connection to the body of the patient 10.

The exposed surface of cover 60 is provided with an adhesive coating 66 of a nonirritant adhesive.

A lead 46 is placed between base 56 and cover 60 and is suitably attached to metallic foil 58 at stud 70.

A removable protective sheet 72 may be placed across the cover 60 and secured thereto by adhesive coating 66. The removable protective sheet 72 assures that the gel-impregnated sponge pad 64 remains moist during storage. The cross-sectional area of the aperture 62 should be sufficient to assure adequate electrical connection with the body of patient 10. Apertures having a diameter of 3, 5 and 9 centimeters have been found effective.

Prior to use, protective sheet 72 is removed, thereby exposing conductive gel-impregnated sponge pad 64 and cover 60 having thereon adhesive coating 66. An electrode 42 is applied to the body of the patient 10, conductive gel-impregnated sponge pad 64 is depressed, ensuring intimate contact with the surface of the body of patient 10.

Referring to FIG. 5, the switch module 40 is mounted on connection circuit 38 at a suitable location remote from the patient 10. Conductors 72 and 74 extend from connector 52 to connector 54. Conductors 72 and 74 are connected to leads 46 and 48, respectively, of the electrode assembly. Both conductors 72 and 74 are routed through switch module 40 from one end to the other. As shown, conductors 72 and 74 may be provided in the form of a self-recoiling cord, if desired.

Each of switches A, B, C and D has a push button which extends through an opening in the side of switch module 40. The switches are of similar construction and during monitoring, switches A, B, C and D are normally open. If defibrillation is desired, operator 22 simultaneously depresses switches A, B, C and D, using both hands, thereby establishing a conductive path from conductor 76 to conductor 78. Monitor/defibrillator 16 is provided with a circuit which is responsive to a conductive path established between conductors 76 and 78. Such circuitry is well known in the art and causes a pulse of energy to be applied through conductors 72 and 74 to electrodes 42 and 44 of the disposable electrode assembly 36. Conductors 76 and 78 may be enclosed within the same sheath as conductors 74 and 76 from switch module 40 to connector 54.

Although switch module 40 is shown to have a generally rectangular cross section, any particular shape may be selected so long as switches A, B, C and D are located so that both hands of the operator 22 are required to simultaneously close the switches, thereby assuring that the operator's hands are remotely positioned from patient 10 during defibrillation.

Also, switch module 40 may be constructed of any durable material and may be potted with a suitable electrically nonconductive material.

A method of monitoring and defibrillating the heart of patient 10 in accordance with the present invention will now be explained. Operator 22 comes to the assistance of patient 10 and adhesively secures electrodes 42 and 44. Although the electrodes 42 and 44 are shown to be secured to the anterior portion of patient 10, one electrode can be easily secured to the posterior portion of the patient to provide for a direct current through the ventricles of the heart in the event that such placement is found to be desirable.

After the operator has secured the electrodes to the patient, connector 50 is secured to connector 52 of connection circuit 38 which is coupled to monitor/defibrillator 16 through connector 54. A conductive path is provided from connection circuit 38 through lead 48 to electrode 44 through the body of patient 10 and electrode 42 to lead 46 and returned to connection circuit 38. This conductive path is suitable for monitoring the heart of patient 10.

If it is desired that the patient 10 receive a pulse of energy for defibrillation, operator 22 simultaneously depresses switches A, B, C and D of switch module 40. This creates a conductive path between conductor 76 and conductor 78 within switch module 40. Monitor/defibrillator 16, responsive to the closing of the switches, causes the pulse of energy to be provided to electrodes 42 and 44 for defibrillation.

I claim:

1. In a system for monitoring and defibrillating the heart of a patient, said system including a monitor/defibrillator, and improved means for connecting the monitor/defibrillator to said patient and for selectively applying a pulse of energy to the patient for defibrillation, comprising:

a first and a second electrode;
   a first conductor for electrically connecting said firs electrode to said monitor/defibrillator;
   a second conductor for electrically connecting said second electrode to said monitor/defibrillator;
   a switch module mounted on but in electrical isolation with said first and second conductors, said switch module positioned on said first and second conductors remotely from said first and second electrodes;
   a third conductor for connecting said switch module to said monitor/defibrillator for establishing a signal indicative of defibrillation when said switch module is actuated;
   means responsive to said signal indicative of defibrillation for causing said monitor/defibrillator to provide said pulse of energy through said first and second electrodes to said patient for defibrillation.

2. The system of claim 1 wherein said switch module includes:

a housing having a generally rectangular cross section formed of two sides, a top and a bottom, wherein said housing has a first and a second end;
   openings located on said sides of said housing;
   an operator-actuated switch extending through each of said openings, said switches connected in series for establishing said signal indicative of defibrillation when said switches are simultaneously depressed; and means located at the first and the second ends of said housing for passing said first conductor therethrough.

3. The system of claim 2 wherein said switch module has two operator-actuated switches located on each of said sides of said switch module housing so that both hands of said operator are required to simultaneously close said switches.

4. The system of claim 2 wherein an inner portion of said housing is potted with an electrically nonconductive material.

5. The system of claim 1 including a single sheath which contains said first, second and third conductors.

6. The system of claim 1 including a connector between said first and second electrodes and said switch module so that said switch module can be easily and quickly removed from said first and second electrodes.

7. The system of claim 1 wherein said first and second electrodes each comprise:
    a base of nonconductive, flexible material;
    a conductive foil secured to the upper surface of said base;
    a cover of flexible, nonconductive material overlying a portion of said base and secured to said upper surface of said base, said cover having an aperture therein, said foil being exposed through said aperture;
    a conductive gel-impregnated sponge pad disposed within said aperture and secured to said foil;
    an adhesive coating applied to the exposed surface of said cover; and
    a lead connected to said foil.

8. The electrode of claim 7 further including a removable protective sheet overlying the adhesive coating and the conductive gel-impregnated sponge pad.

9. The electrode of claim 7 wherein the sponge pad has a diameter of at least 3 centimeters for assuring a good electrical connection with the patient when said pulse of energy is provided to said patient.

10. The electrode of claim 7 wherein said aperture defines a generally circular area overlying the foil.

11. In an operator-controlled system for defibrillating the heart of a patient by the application of a pulse of energy applied to the heart, the improvement comprising:
    a first and a second electrode adapted to be secured to the patient, thereby obviating the need for the hands of said operator to be proximate said patient; and
    a switch module having a top, a bottom, two sides and two ends located remotely from said electrodes and having four operator-actuated switches therein which, when simultaneously actuated, cause the system to apply said pulse of energy to said first and second electrodes, two of said switches positioned on each of said side of said module so that both hands of said operator are required to simultaneously close said switches, thereby assuring that said hands of said operator remain remotely positioned from said electrodes during defibrillation.

12. The system of claim 11 including a first and second conductor which connects said first and second electrodes, respectively, to said system for defibrillating, said switch module being mounted on said conductors.

13. A system for connecting a monitor/defibrillator to a patient for monitoring the heart and for providing a pulse of energy to the heart for defibrillation thereof, comprising:
    a monitor/defibrillator;
    an electrode assembly including:
        a first and a second electrode similarly constructed and each having
            a base of nonconductive flexible material;
            a conductive foil secured to the upper surface of said base;
            a cover of flexible nonconductive material overlying a portion of said base and secured to the upper surface of said base, said cover having an aperture therein, and said foil being exposed through said aperture;
            a conductive gel-impregnated sponge disposed within said aperture;
            an adhesive coating applied to the exposed surface of said cover;
            an electrical lead connected to said foil; and
            a removable protective sheet overlying the adhesive coating and said conductive gel-impregated sponge; and
    a first connector means coupled to the lead from each electrode;
    a second connector means coupled to the first connector means;
    a first conductor for electrically connecting said second connector means and said monitor/defibrillator;
    a switch module mounted on said first conductor remotely from said electrodes and having a plurality of operator-actuated switches connected in series with each other;
    a second conductor connecting said plurality of switches connected in series with each other to said monitor/defibrillator for providing a signal indicative of defibrillation when said switches are simultaneously actuated; and
    means responsive to said signal for applying the pulse of energy to the heart for defibrillation thereof.

14. A method of monitoring the heart of a patient and defibrillating said heart by applying a pulse of energy to said patient, comprising:
    adhesively securing a first and a second electrode to the patient;
    connecting said first and second electrodes to a monitor/defibrillator through a switch module having a plurality of operator-actuated switches positioned remotely from said electrodes;
    monitoring the heart of said patient;
    actuating said plurality of operator-actuated switches simultaneously when it is required to apply a pulse of energy to said patient;
    providing a connection between said switch module and said monitor/defibrillator for establishing a signal indicative of defibrillation when said plurality of switches are actuated; and
    providing said pulse of energy to said electrodes in response to said signal indicative of defibrillation.

* * * * *